US012654002B2

(12) United States Patent
Trivedi et al.

(10) Patent No.: US 12,654,002 B2
(45) Date of Patent: Jun. 16, 2026

(54) ELECTRODE LEADS HAVING NERVE CUFFS AND ASSOCIATED SYSTEMS AND METHODS

(71) Applicant: The Alfred E. Mann Foundation for Scientific Research, Valencia, CA (US)

(72) Inventors: Hemang Trivedi, Valencia, CA (US); William Andrew Brandt, Castaic, CA (US); Sahar Elyahoodayan, Los Angeles, CA (US); Christopher Reed Jenney, Valencia, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 318 days.

(21) Appl. No.: 18/468,730

(22) Filed: Sep. 17, 2023

(65) Prior Publication Data

US 2024/0108883 A1     Apr. 4, 2024

Related U.S. Application Data

(60) Provisional application No. 63/411,213, filed on Sep. 29, 2022.

(51) Int. Cl.
*A61N 1/05*          (2006.01)
*A61N 1/36*          (2006.01)
(52) U.S. Cl.
CPC ......... *A61N 1/0556* (2013.01); *A61N 1/3606* (2013.01)
(58) Field of Classification Search
CPC ............................. A61N 1/3606; A61N 1/0556
See application file for complete search history.

(56) References Cited

U.S. PATENT DOCUMENTS

| | | | |
|---|---|---|---|
| 4,573,481 A | 3/1986 | Bullara | |
| 4,602,624 A | 7/1986 | Naples et al. | |

(Continued)

FOREIGN PATENT DOCUMENTS

| | | |
|---|---|---|
| CN | 112402786 A | 2/2021 |
| WO | WO 2008092246 A1 | 8/2008 |

(Continued)

OTHER PUBLICATIONS

PCT International Search and Written Opinion dated Dec. 19, 2023 for PCT App. Ser. No. PCT/US2023/074422.
(Continued)

*Primary Examiner* — Alyssa M Alter
(74) *Attorney, Agent, or Firm* — Henricks Slavin LLP

(57)          ABSTRACT

An electrode lead includes an elongate lead body and a nerve cuff. The nerve cuff may include a cuff body, with a front layer and a rear layer, affixed to the distal end of the lead body and a plurality of electrically conductive members located between the front and rear layers. Each of the electrically conductive member defines a front side, a rear side and an outer perimeter and may include a plurality of holes that extend from the front side to the rear side and that are located around the outer perimeter. The cuff body front layer includes a plurality of windows that are respectively aligned with and located inwardly of the outer perimeters of the electrically conductive members, and a plurality of window frames that extend from the windows to the outer perimeters of the electrically conductive members. The cuff body also includes a plurality of anchors that respectively extend through the electrically conductive member holes and connect the window frames to the cuff body rear layer.

12 Claims, 8 Drawing Sheets

(56) References Cited

U.S. PATENT DOCUMENTS

| | | | |
|---|---|---|---|
| 4,940,065 | A | 7/1990 | Tanagho et al. |
| 5,251,634 | A | 10/1993 | Weinberg |
| 5,400,784 | A | 3/1995 | Durand et al. |
| 5,439,485 | A | 8/1995 | Mar et al. |
| 5,487,756 | A | 1/1996 | Kallesoe et al. |
| 5,634,462 | A | 6/1997 | Tyler et al. |
| 5,919,220 | A | 7/1999 | Stieglitz et al. |
| 6,066,165 | A | 5/2000 | Racz |
| 6,093,197 | A | 7/2000 | Bakula et al. |
| 6,210,339 | B1 | 4/2001 | Kiepen et al. |
| 6,292,703 | B1 | 9/2001 | Meier et al. |
| 7,383,090 | B2 | 6/2008 | O'Brien et al. |
| 7,499,742 | B2 | 3/2009 | Bolea et al. |
| 7,794,256 | B1 | 9/2010 | Sochor |
| 7,809,442 | B2 | 10/2010 | Bolea et al. |
| 7,813,812 | B2 | 10/2010 | Kieval et al. |
| 7,996,092 | B2 | 8/2011 | Mrva et al. |
| 8,116,882 | B2 | 2/2012 | Kowalczewski |
| 8,155,757 | B1 | 4/2012 | Neisz et al. |
| 8,224,449 | B2 | 7/2012 | Carbunaru et al. |
| 8,311,645 | B2 | 11/2012 | Bolea et al. |
| 8,340,785 | B2 | 12/2012 | Bonde et al. |
| 8,660,665 | B2 | 2/2014 | Walter et al. |
| 8,792,973 | B2 | 7/2014 | Moran et al. |
| 8,934,992 | B2 | 1/2015 | Johnson et al. |
| 9,186,511 | B2 | 11/2015 | Bolea |
| 9,227,053 | B2 | 1/2016 | Bonde et al. |
| 9,486,628 | B2 | 11/2016 | Christopherson et al. |
| 9,549,708 | B2 | 1/2017 | Mercanzini et al. |
| 9,603,538 | B2 | 3/2017 | Fisher et al. |
| 9,849,288 | B2 | 12/2017 | Meadows et al. |
| 9,889,304 | B2 | 2/2018 | Mercanzini |
| 9,931,045 | B2 | 4/2018 | Brunnett et al. |
| 10,758,723 | B2 | 9/2020 | Fang et al. |
| 11,833,348 | B2 | 12/2023 | Brandt et al. |
| 12,194,290 | B2 | 1/2025 | Dearden et al. |
| 12,296,172 | B2 | 5/2025 | Jenny et al. |
| 12,350,489 | B2 | 7/2025 | Jenny et al. |
| 2002/0198582 | A1 | 12/2002 | Edell et al. |
| 2005/0070982 | A1 | 3/2005 | Heruth et al. |
| 2005/0186829 | A1 | 8/2005 | Balsells |
| 2006/0004430 | A1 | 1/2006 | Rossing et al. |
| 2006/0030919 | A1 | 2/2006 | Mrva et al. |
| 2007/0123765 | A1 | 5/2007 | Hetke et al. |
| 2007/0185542 | A1 | 8/2007 | Bolea et al. |
| 2008/0082137 | A1 | 4/2008 | Kieval et al. |
| 2008/0103545 | A1 | 5/2008 | Bolea et al. |
| 2008/0172101 | A1 | 7/2008 | Bolea et al. |
| 2009/0132042 | A1 | 5/2009 | Hetke et al. |
| 2009/0210042 | A1 | 8/2009 | Kowalczewski |
| 2010/0305674 | A1 | 12/2010 | Zarembo et al. |
| 2010/0331933 | A1 | 12/2010 | Carbunaru et al. |
| 2011/0066196 | A1 | 3/2011 | Alexander et al. |
| 2011/0130815 | A1 | 6/2011 | Gibson et al. |
| 2011/0154655 | A1 | 6/2011 | Hetke et al. |
| 2011/0251473 | A1 | 10/2011 | Moran et al. |
| 2011/0301665 | A1 | 12/2011 | Mercanzini et al. |
| 2012/0089153 | A1 | 4/2012 | Christopherson et al. |
| 2012/0150255 | A1 | 6/2012 | Lindenthaler et al. |
| 2012/0154256 | A1 | 6/2012 | Grover et al. |
| 2012/0277819 | A1 | 11/2012 | Cowley et al. |
| 2012/0316417 | A1 | 12/2012 | Vetter |
| 2013/0030352 | A1 | 1/2013 | Seymour et al. |
| 2013/0085361 | A1 | 4/2013 | Mercanzini et al. |
| 2013/0090711 | A1 | 4/2013 | Ramachandran et al. |
| 2013/0150938 | A1 | 6/2013 | Carbunaru et al. |
| 2013/0304174 | A1 | 11/2013 | Langhals et al. |
| 2014/0005763 | A1 | 1/2014 | Cederna et al. |
| 2014/0058482 | A1 | 2/2014 | Gupta et al. |
| 2014/0163659 | A1 | 6/2014 | Boling |
| 2014/0188202 | A1 | 7/2014 | Zarembo et al. |
| 2014/0228905 | A1 | 8/2014 | Bolea |
| 2014/0303703 | A1 | 10/2014 | Mercanzini et al. |
| 2015/0119673 | A1 | 4/2015 | Pellinen et al. |
| 2015/0128413 | A1 | 5/2015 | Vetter et al. |
| 2015/0157854 | A1 | 6/2015 | Hetke et al. |
| 2015/0174396 | A1 | 6/2015 | Fisher et al. |
| 2015/0224307 | A1 | 8/2015 | Bolea |
| 2015/0374975 | A1 | 12/2015 | Callegari et al. |
| 2016/0184581 | A1 | 6/2016 | Bonde et al. |
| 2016/0199637 | A1 | 7/2016 | Xu et al. |
| 2016/0287863 | A1 | 10/2016 | Mercanzini et al. |
| 2016/0331326 | A1 | 11/2016 | Xiang et al. |
| 2016/0331994 | A1 | 11/2016 | Smith et al. |
| 2017/0021163 | A1 | 1/2017 | Westlund et al. |
| 2017/0225004 | A1 | 8/2017 | Casse et al. |
| 2017/0266436 | A1 | 9/2017 | Suwito et al. |
| 2017/0319846 | A1 | 11/2017 | Plachta et al. |
| 2018/0117313 | A1* | 5/2018 | Schmidt ............... A61N 1/3752 |
| 2018/0132790 | A1 | 5/2018 | Yao et al. |
| 2018/0221660 | A1 | 8/2018 | Suri et al. |
| 2018/0318577 | A1 | 11/2018 | Ng et al. |
| 2018/0318578 | A1 | 11/2018 | Ng et al. |
| 2019/0060646 | A1 | 2/2019 | Ng et al. |
| 2019/0069949 | A1 | 3/2019 | Vrba et al. |
| 2019/0282805 | A1 | 9/2019 | Schmidt et al. |
| 2020/0069935 | A1 | 3/2020 | Johnson et al. |
| 2020/0083922 | A1 | 3/2020 | Hong et al. |
| 2020/0146583 | A1 | 5/2020 | Hestad et al. |
| 2020/0230412 | A1 | 7/2020 | Rondoni et al. |
| 2020/0230421 | A1 | 7/2020 | Zaidi et al. |
| 2020/0306526 | A1 | 10/2020 | Doguet et al. |
| 2021/0085964 | A1 | 3/2021 | Zaidi et al. |
| 2021/0205662 | A1 | 7/2021 | Lu et al. |
| 2022/0062629 | A1 | 3/2022 | Dearden |
| 2022/0088374 | A1 | 3/2022 | Ackermann et al. |
| 2022/0184387 | A1 | 6/2022 | Searfoss et al. |
| 2022/0313987 | A1 | 10/2022 | Jenny et al. |
| 2023/0010510 | A1 | 1/2023 | Brandt et al. |
| 2023/0241394 | A1 | 8/2023 | Jenny et al. |
| 2024/0009452 | A1 | 1/2024 | Jenny et al. |
| 2024/0058602 | A1 | 2/2024 | Brandt et al. |
| 2025/0121182 | A1 | 4/2025 | Dearden et al. |
| 2025/0182934 | A1 | 6/2025 | Jenny et al. |
| 2025/0205478 | A1 | 6/2025 | Jenny et al. |
| 2025/0256093 | A1 | 8/2025 | Jenny |
| 2025/0276174 | A1 | 9/2025 | Jenny |
| 2025/0303146 | A1 | 10/2025 | Jenny et al. |

FOREIGN PATENT DOCUMENTS

| | | |
|---|---|---|
| WO | WO 2009045772 A1 | 4/2009 |
| WO | WO 2012154256 A1 | 11/2012 |
| WO | WO 2013188871 A1 | 12/2013 |
| WO | WO 2016039768 A1 | 3/2016 |
| WO | WO 2020182293 A1 | 9/2020 |
| WO | WO 2021108810 A1 | 6/2021 |

OTHER PUBLICATIONS

U.S. Appl. No. 17/463,611, filed Sep. 1, 2021, 20220062629 A1
U.S. Appl. No. 17/463,630, filed Sep. 1, 2021, U.S. Pat. No. 11,833,348 B2.
U.S. Appl. No. 18/495,503, filed Oct. 26, 2023, 20240058602 A1.
U.S. Appl. No. 17/683,598, filed Mar. 1, 2022, 20220313987 A1.
U.S. Appl. No. 17/710,570, filed Mar. 31, 2022, 20230241394 A1.
U.S. Appl. No. 18/186,927, filed Mar. 20, 2023, 20240009452 A1.
U.S. Appl. No. 18/968,650, filed Dec. 4, 2024.
U.S. Appl. No. 18/981,465, filed Dec. 14, 2024, 20250121182 A1.
U.S. Appl. No. 19/019,360, filed Jan. 13, 2025.
U.S. Appl. No. 18/939,479, filed Nov. 6, 2024.
U.S. Appl. No. 18/985,448, filed Dec. 18, 2024.
U.S. Appl. No. 19/034,472, filed Jan. 22, 2025.
U.S. Appl. No. 17/463,630, filed Sep. 1, 2021, 20230010510 A1.
U.S. Appl. No. 18/186,927, filed Mar. 20, 2023.

* cited by examiner

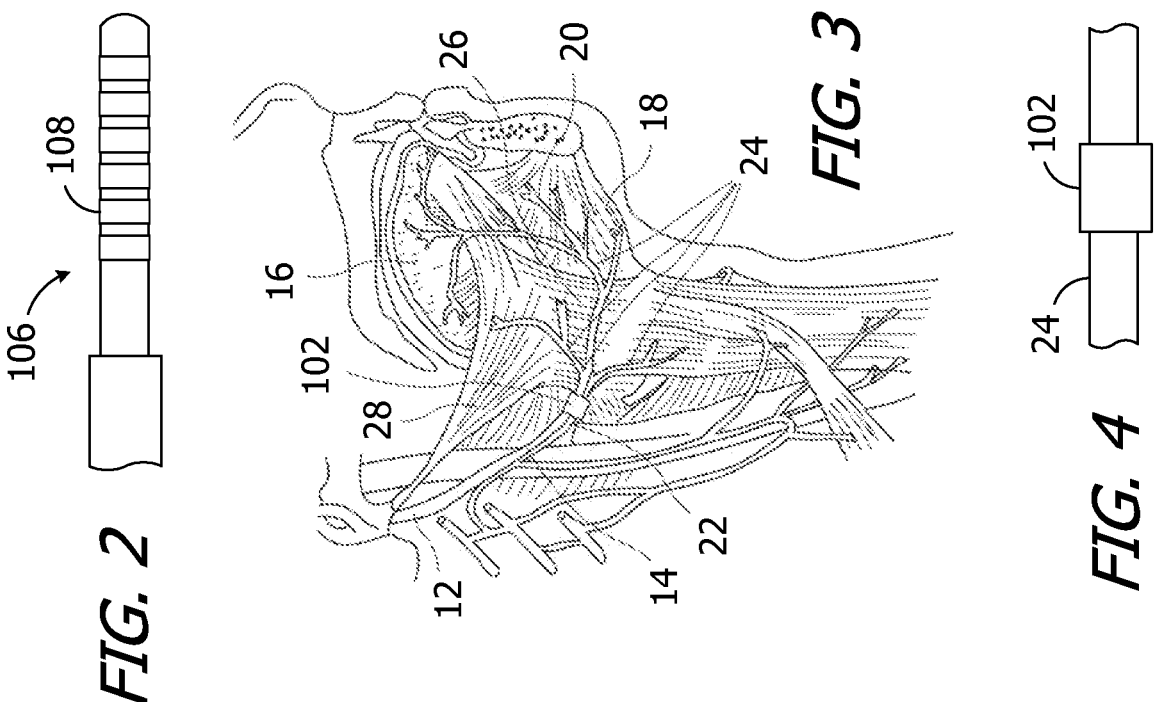
*FIG. 2*
*FIG. 3*
*FIG. 4*
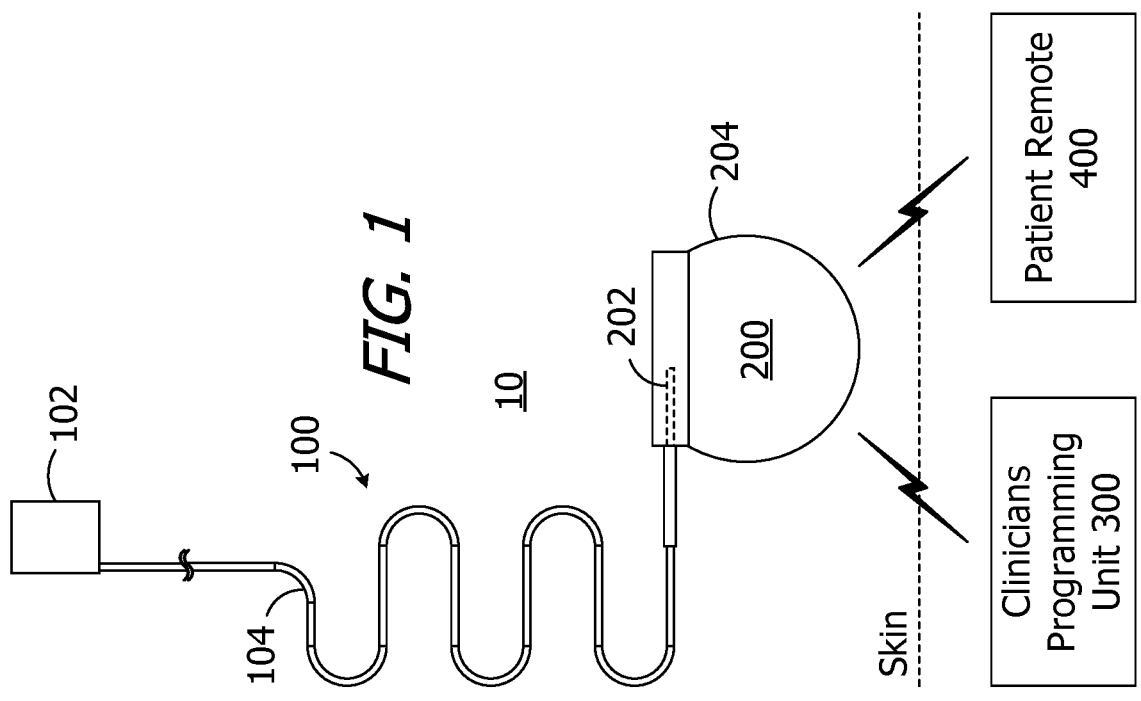
*FIG. 1*

ELECTRODE LEADS HAVING NERVE CUFFS AND ASSOCIATED SYSTEMS AND METHODS

CROSS-REFERENCE TO RELATED APPLICATION

This application claims the benefit of U.S. Provisional Application No. 63/411,213, filed Sep. 29, 2022, and entitled "Electrode Leads Having Nerve Cuffs and Associated Systems and Methods," which is incorporated herein by reference.

BACKGROUND OF THE INVENTIONS

1. Field of Inventions

The present inventions relate generally to the treatment of obstructive sleep apnea by stimulating the hypoglossal nerve.

2. Description of the Related Art

Obstructive sleep apnea (OSA) is a highly prevalent sleep disorder that is caused by the collapse of or increase in the resistance of the pharyngeal airway, often resulting from tongue obstruction. The obstruction of the upper airway is mainly caused by reduced genioglossus muscle (GM) activity during the deeper states of non-rapid eye movement (NREM) sleep. In some OSA patients, obstruction occurs predominantly during rapid eye movement (REM) sleep. This is known as REM OSA and has different cardiometabolic and neurocognitive risks. Obstruction of the upper airway causes breathing to pause during sleep. Cessation of breathing, in turn, causes a decrease in the blood oxygen saturation level, which is eventually corrected when the person wakes up and resumes breathing. The long-term effects of OSA include, but are not limited to, high blood pressure, heart failure, strokes, diabetes, headaches, and general daytime sleepiness and memory loss.

Some proposed methods of alleviating apneic events involve the use of neurostimulators to open the upper airway. Such therapy involves stimulating the nerve fascicles of the hypoglossal nerve (HGN) that innervate the intrinsic and extrinsic muscles of the tongue in a manner that prevents retraction of the tongue, which would otherwise close the upper airway during the inspiration portion of the respiratory cycle. In some instances, the trunk of the HGN is stimulated with a nerve cuff, including a cuff body and a plurality of electrically conductive contacts (sometimes referred to as "electrodes") on the cuff body, that is positioned around the HGN trunk. To that end, some nerve cuffs are pre-shaped to a furled state, may assume slightly less furled states, and may be unfurled to a flattened state. The HGN trunk nerve cuff may be configured in such a manner that it can be used to selectively stimulate nerve fascicles which innervate muscles that extend the tongue, while avoiding other nerve fascicles, with what is predominantly radial vector stimulation. HGN branches may also be stimulated. For example, an HGN GM branch may be stimulated with what is predominantly axial vector stimulation.

The contacts of at least some nerve cuffs are defined by electrically conductive members that are located between two non-conductive layers, i.e., a relatively thin front layer and a relatively thick rear layer, with the front layer including openings (or "windows") that expose portions of the conductive members. The portions of window-containing layer that cover the remainders of the conductive members, and that border the windows, are referred to herein as "window frames."

Exemplary nerve cuffs are illustrated and described in U.S. Pat. Pub. Nos. 2018/0318577A1, 2018/0318578A1, 2019/0060646A1 and 2019/0282805A1, which are incorporated herein by reference in their entirety.

SUMMARY

The present inventors have determined that nerve cuffs are susceptible to improvement. In particular, the present inventors have determined that certain electrically conductive materials with otherwise desirable properties (e.g., platinum-iridium) do not bond well with non-conductive materials that have desirable mechanical properties (e.g., silicone) or, when employed, the adhesive (e.g., silicone adhesive) that is used to bond non-conductive layers that are formed from materials that have desirable mechanical properties. The less than optimal bond, coupled with the thinness of the window frames and the stress that is applied to the conductive members when the nerve cuff is in a furled state, may cause delamination of the nerve cuff at the window frames and, in some instances, dislodgement of the conductive members. As such, the present inventors have determined that it would be desirable to provide nerve cuffs that, among other things, reduce the likelihood of delamination at the window frames.

An electrode lead in accordance with at least one of the present inventions includes an elongate lead body and a nerve cuff. The nerve cuff may include a cuff body, with a front layer and a rear layer, affixed to the distal end of the lead body and a plurality of electrically conductive members located between the front and rear layers. Each of the electrically conductive member defines a front side, a rear side and an outer perimeter and may include a plurality of holes that extend from the front side to the rear side and that are located around the outer perimeter. The cuff body front layer includes a plurality of windows that are respectively aligned with and located inwardly of the outer perimeters of the electrically conductive members, and a plurality of window frames that extend from the windows to the outer perimeters of the electrically conductive members. The cuff body also includes a plurality of anchors that respectively extend through the electrically conductive member holes and connect the window frames to the cuff body rear layer.

The present inventions also include systems with an implantable pulse generator or other implantable stimulation device in combination with such an electrode lead.

BRIEF DESCRIPTION OF THE DRAWINGS

Detailed descriptions of exemplary embodiments will be made with reference to the accompanying drawings.

FIG. 1 is a plan view of a stimulation system in accordance with one embodiment of a present invention.

FIG. 2 is a plan view of a portion of the stimulation system illustrated in FIG. 1.

FIG. 3 is a cut-away anatomical drawing of the head and neck area illustrating the muscles that control movement of the tongue, the HGN and its branches that innervate these muscles, and the nerve cuff illustrated in FIG. 1 on the HGN trunk.

FIG. 4 is a plan view showing the nerve cuff illustrated in FIG. 1 on the HGN GM branch.

DETAILED DESCRIPTION OF THE EXEMPLARY EMBODIMENTS

Figures 5, 6:
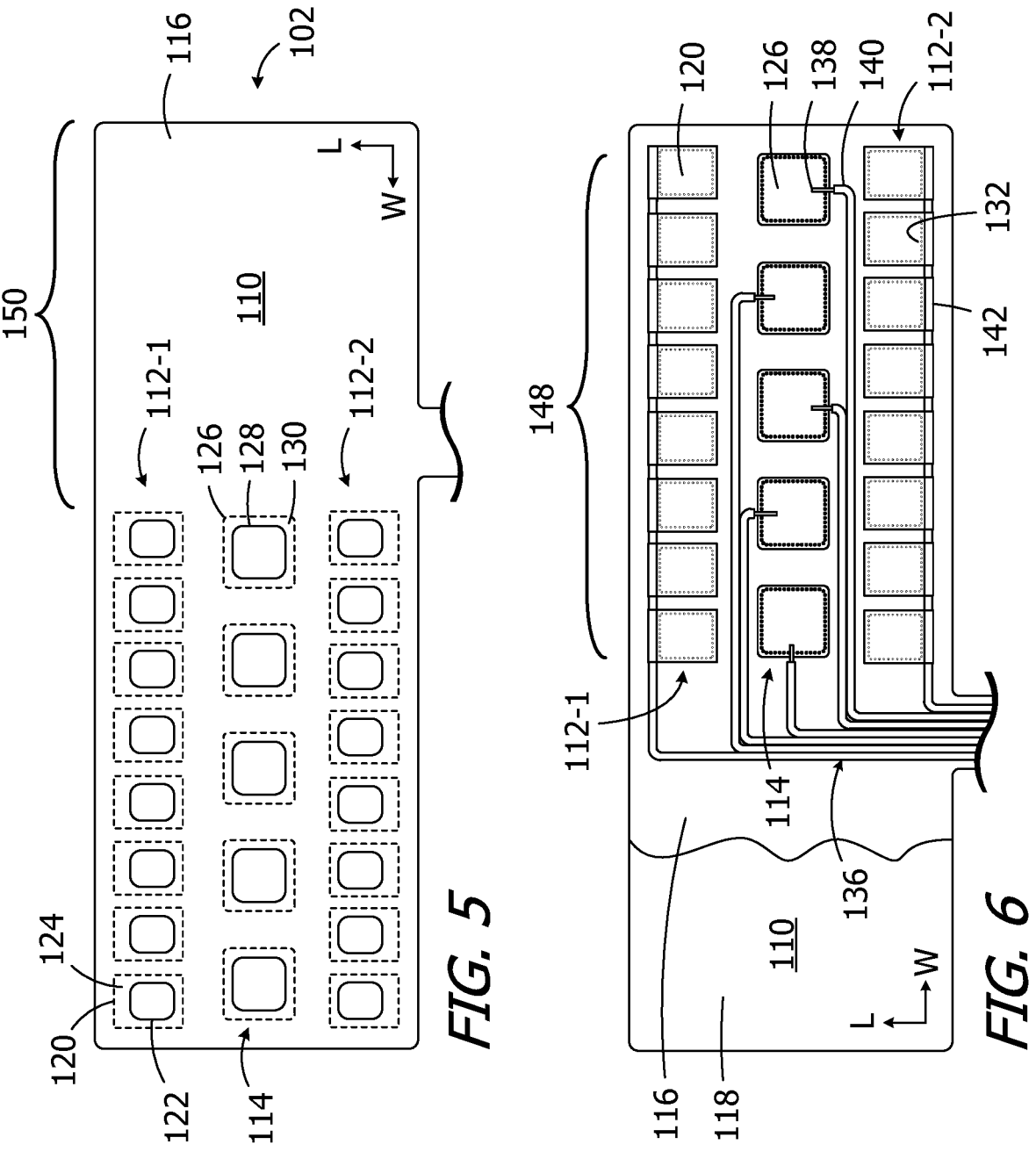
FIG. 5 is a front view of the nerve cuff illustrated in FIG. 1 in an unfurled state.
FIG. 6 is a rear, cutaway view of the nerve cuff illustrated in FIG. 1 in an unfurled state.

The following is a detailed description of the best presently known modes of carrying out the inventions. This description is not to be taken in a limiting sense, but is made merely for the purpose of illustrating the general principles of the inventions.

Referring to FIGS. 1 and 2, a stimulation system 10 in accordance with one embodiment of a present invention includes an electrode lead 100 and an implantable stimulator such as the implantable pulse generator ("IPG") 200. A clinician's programming unit 300, a patient remote 400 and/or an IPG charger (not shown) may also be provided in some instances. The exemplary electrode lead 100 includes a nerve cuff 102 and a lead body 104 that couples the nerve cuff 102 to the IPG 200 by way of lead connector 106, with a plurality contacts 108, on the proximal end of the lead body 104 and a corresponding connector receptacle 202 on the IPG 200. The nerve cuff 102 is configured in such a manner that it may be circumferentially disposed around either the HGN trunk or a HGN branch (e.g., the HGN GM branch) as is discussed below with reference to FIGS. 3 and 4. The lead body 104 may include one or more S-shaped sections in order to provide strain relief (as shown) or may be straight. The S-shaped sections accommodate body movement at the location within the neck where the lead body 104 is implanted, thereby reducing the likelihood that the HGN will be damaged due to unavoidable pulling of the electrode lead 100 that may result from neck movements. The accommodation provided by the S-shaped sections also reduces the likelihood of fatigue damage. Additionally, although the exemplary system 10 includes a single electrode lead 100, other embodiments may include a pair of electrode leads 100 for bilateral HGN stimulation and an IPG (not shown) with two connector receptacles.

Turning to FIG. 3, and as alluded to above, the nerve cuff 102 may be positioned around the trunk 14 of the HGN 12 and used to stimulate the muscles that anteriorly move the tongue 16 and, in particular, the fascicles of the HGN 12 that innervate the tongue protrusor muscles, such as the genioglossus 18 and/or the geniohyoid muscles 20. The nerve cuff 102 is positioned on the HGN trunk 14 at a position 22 proximal to the HGN branches 24. Although there are advantages to implanting the nerve cuff 102 at this proximal position 22, i.e., reduced surgical time and effort as well as reduced risk and trauma to the patient, it introduces the problem of inadvertently stimulating other fascicles of the HGN trunk 14 that innervate muscles in opposition to the genioglossus 18 and/or the geniohyoid muscles 20, i.e., the tongue retractor muscles, e.g., the hyoglossus 26 and styloglossus muscles 28, as well as the intrinsic muscles of the tongue 16. Accordingly, while some clinicians may desire to stimulate the HGN 12 at the HGN trunk 14, others may desire to stimulate the HGN at the GM branch 24. As illustrated in FIG. 4, the same nerve cuff 102 is configured in such a manner that it may be positioned the HGN GM branch 24 instead of the trunk 14.

Figure 9:
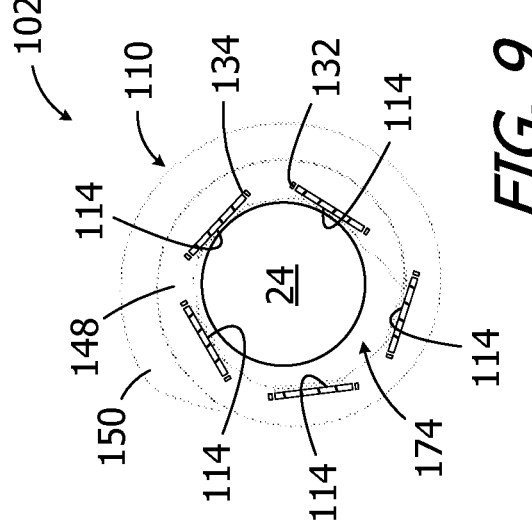
FIG. 9 is a section view of the nerve cuff illustrated in FIG. 1 in a furled state around a HGN branch.

The exemplary nerve cuff 102 is shown in a flattened, unfurled state in FIGS. 5 and 6 and is shown in a furled (or "curled") state in FIG. 9. In the illustrated implementation, the nerve cuff 102 is pre-set (or "pre-shaped") to the furled state and an external force may be used to partially or completely unfurl the nerve cuff 102. The nerve cuff 102 will return to the pre-shaped furled state when the force is removed and, as discussed below, may assume a variety furled states depending on the size of the HGN trunk or HGN branch that the nerve cuff 102 is placed around. Various examples of nerve cuffs that are capable of assuming different sizes are disclosed in aforementioned U.S. Pat. Pub. No. 2019/0060646A1.

Referring first to FIGS. 5 and 6, the nerve cuff 102 includes a cuff body 110 that defines a length L and a width W that is greater than the length, first and second pluralities of electrically conductive contacts (or "contacts") 112-1 and 112-2 on the cuff body 110, and a plurality of electrically conductive contacts (or "contacts") 114. The contacts 112-1 are spaced from one another in the length direction, as are the contacts 112-2. Contacts 112-1, 112-2 and 114 may also be referred to as "electrodes." The contacts 112-1 are connected to one another in series and function as a single relatively wide contact. The contacts 112-2 are also connected to one another in series and function as a single relatively wide contact. The contacts 114 are not connected to one another in series and, as compared to the each of the pluralities of contacts 112-1 and 112-2, the contacts 114 are relatively narrow. Although the number may increase or decrease in the context of other nerve applications, at least five contacts 114 may be spaced from one another in the width direction and located between the electrically conductive contacts 112-1 and 112-2 (collectively "contacts 112"), and there are five relatively narrow contacts 114 in the illustrated embodiment. As used herein, "relatively wide" structures are structures that are longer in the width direction than structures that are referred to as "relatively narrow" and "relatively narrow" structures are structures that are shorter in the width direction than structures that are referred to as "relatively wide."

In the implementation illustrated in FIGS. 5 and 6, the contacts 114 are centered relative to the contacts 112-1 and 112-2 and are aligned with one another in the length direction. In other implementations, the contacts may be non-centered relative to the relatively wide contacts 112-1 and 112-2 and/or offset from one another in the length direction. With respect to shape, and although the present inventions are not so limited, the individual contacts 112 are in the shape of rectangles with rounded corners, while the contacts 114 are squares with rounded corners. Other exemplary shapes are discussed below.

Figures 14, 15, 16, 17:
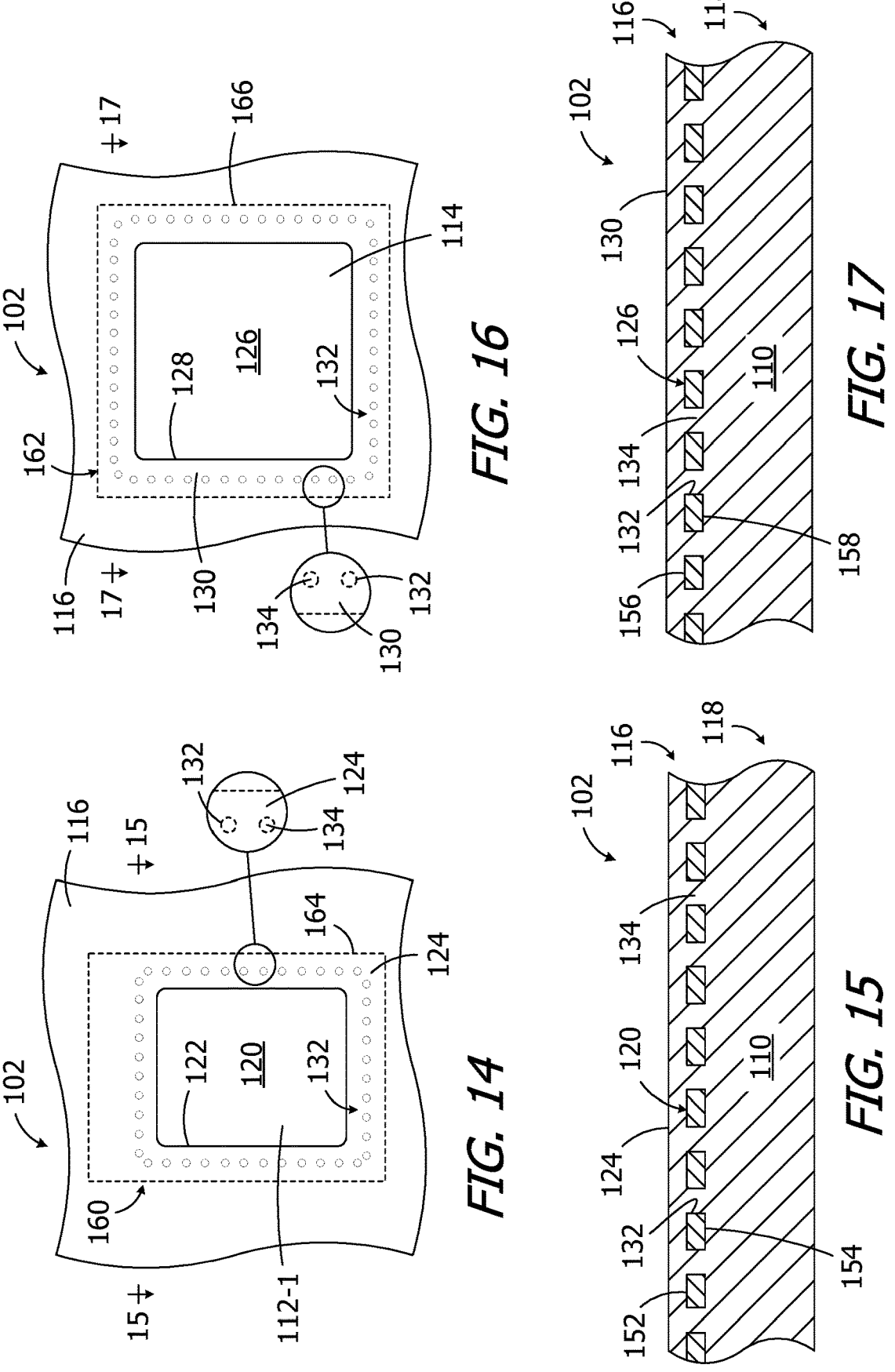
FIG. 14 is a front view of a portion of the nerve cuff illustrated in FIG. 1.
FIG. 15 is a section view taken along line 15-15 in FIG. 14.
FIG. 16 is a front view of a portion of the nerve cuff illustrated in FIG. 1.
FIG. 17 is a section view taken along line 17-17 in FIG. 16.

The cuff body 110 in the exemplary implementation may include a front layer 116 that will face the HGN trunk or branch and a rear layer 118 that will face away from the HGN trunk or branch. A plurality of conductive members 120, which form the contacts 112, are located between the front layer 116 and rear layer 118. The plurality of conductive members 120 are exposed by way of a plurality of windows 122 in the cuff body front layer 116. As discussed in greater detail below, the windows 122 are located inwardly of the outer perimeter (and outer edges) of the conductive members 120, which are shown in dashed lines in FIG. 5, and the exposed portions of the conductive members define the contacts 112. The portions of the front layer 116 that are located between the windows 122 and the outer perimeters (and outer edges) of the conductive members 120 define window frames 124 that hold the conductive members 120 against the rear layer 118 and between front and rear layers 116 and 118. Similarly, a plurality of conductive members 126, which form the contacts 114, are located between the front layer 116 and rear layer 118. The plurality of conductive members 126 are exposed by way of a plurality of windows 128 in the cuff body front layer 116. The windows 128 are located inwardly of the outer perimeter of the conductive members 126, which are shown in dashed lines in FIG. 5, and the exposed portions of the conductive members define the contacts 114. The portions of the front layer 116 that are located between the windows 128 and the outer perimeters (and outer edges) of the conductive members 126 define window frames 130 that hold the conductive members 126 against the rear layer 118 and between the front and rear layers 116 and 118. The respective pluralities of holes 132 in each conductive member 120 and 126, which are coextensive with the associated window frames 124 and 130, extend completely through the conductive members 120 and 126 of the contacts 112 and 114 and facilitate the formation of window frame anchors 134 in the manner described below with reference to FIGS. 15 and 17.

Figure 8:
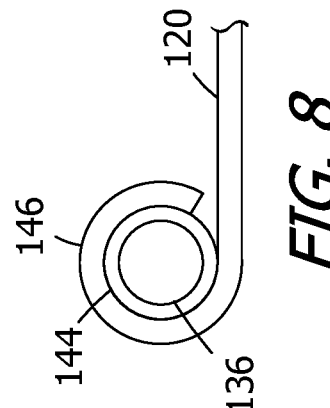
FIG. 8 is a side view of a portion of the nerve cuff illustrated in FIG. 1 prior to crimping.
Figure 7:
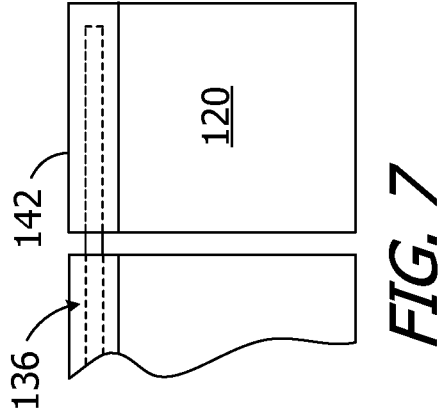
FIG. 7 is a rear view of a portion of the nerve cuff illustrated in FIG. 1.
Figures 10, 11, 12, 13:
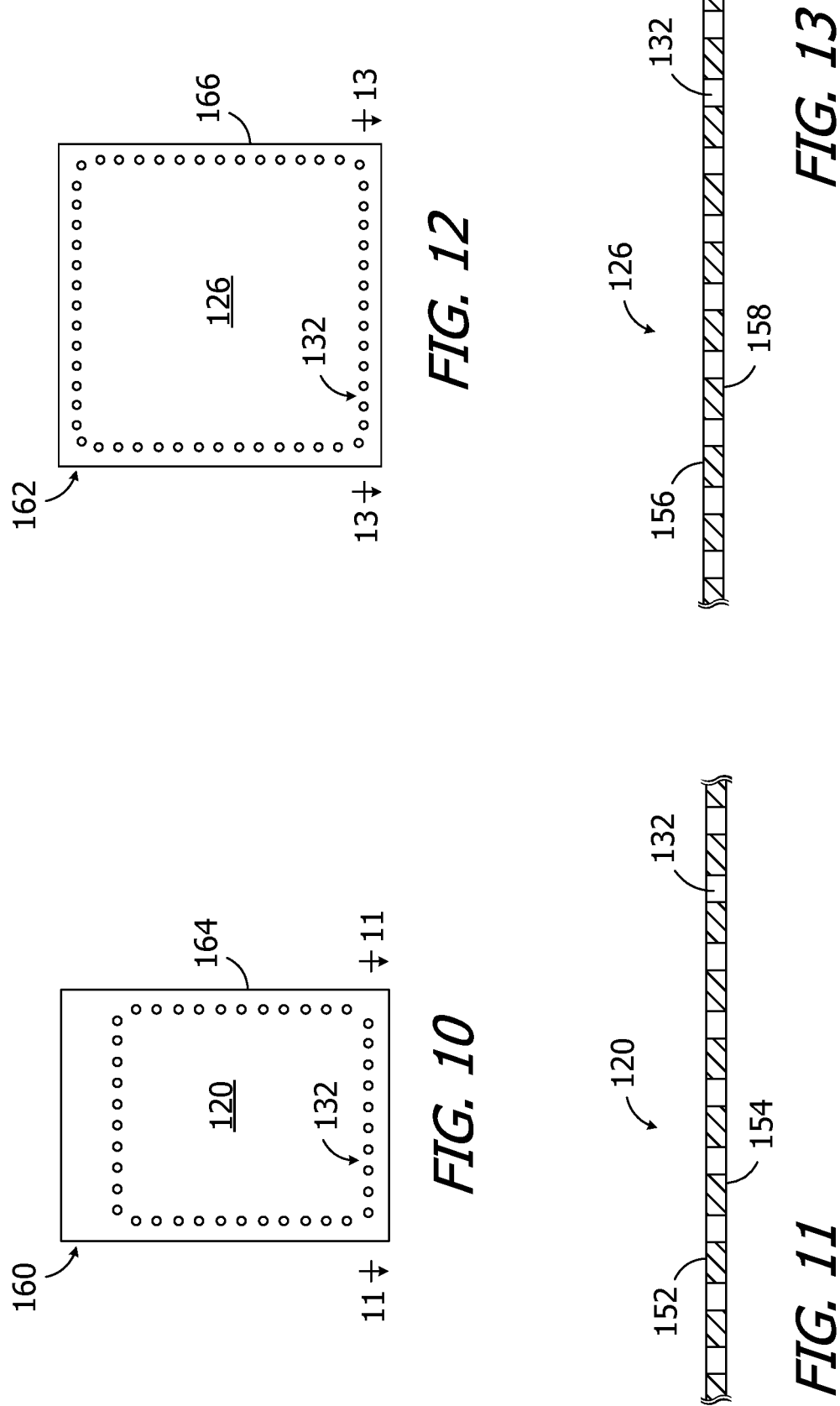
FIG. 10 is a front view of a portion of the nerve cuff illustrated in FIG. 1.
FIG. 11 is a section view taken along line 11-11 in FIG. 10.
FIG. 12 is a front view of a portion of the nerve cuff illustrated in FIG. 1.
FIG. 13 is a section view taken along line 13-13 in FIG. 12.

The contacts 112 and 114 in the illustrated embodiment may be individually electrically connected to the plurality contacts 108 on the lead connector 106 (FIG. 2) by wires or cables 136 (FIG. 6) that extend through the lead body 104. Each wire 136 in the exemplary embodiment includes a conductor 138 and an insulator 140. The conductors 138, which may be in the form of a wire or a cable, may be connected to the rear side of the conductive members 120 and 126 by any suitable process. For example, and referring to FIGS. 6 and 7, each of the conductive members 120 of the contacts 112-1 and 112-2 includes a crimp region 142, and the portions of the associated wires 136 are crimped to the conductive members 120 at the crimp regions. With respect to the crimping process, crimp tubes 144 (FIG. 8) may be provided at spaced locations along the wires 136 and the conductive members 120 may be provided with rolled portions 146 through which the wires and crimp tubes are passed prior to crimping and the formation of the crimp regions 142. The portions of the insulators 140 within the crimp regions may be removed prior to crimping or simply squeezed out of the resulting joint during the crimping process. Other exemplary methods of securing the conductors 138 to conductive members 120 include, but are not limited to, forming joints by welding and combined welding/crimping processes. To that end, the conductors 138 are welded to the conductive members of the contacts 114 in the exemplary implementation, as shown in FIG. 6.

As is also illustrated in FIGS. 5 and 6, the cuff body 110 in the exemplary implementation includes a stimulation region 148 and a compression region 150. The contacts 112 and 114 are located within the stimulation region 148 and there are no contacts located within the compression region 150. The compression region 150 wraps around at least a portion of the stimulation region 148 when the nerve cuff 102 is in the pre-shaped furled state as well as in sightly larger, expanded and less tightly furled states, thereby resisting (but not preventing) expansion of the stimulation region and improving the electrical connection between the contacts 112 and 114 and the HGN. As a result, the exemplary nerve cuff 102 may be positioned around an HGN branch 24, as shown in FIG. 9, or the HGN trunk.

As illustrated for example in FIGS. 10-13, and as alluded to above, the exemplary conductive members 120 and 126 each include a plurality of holes 132. In particular, a plurality of holes 132 extend completely through the conductive member 120, from the front side 152 to the rear side 154, and a plurality of holes 132 extend completely through conductive member 126, from the front side 156 to the rear side 158. The front sides face the nerve, and the rear sides face away from the nerve. The holes 132 are coextensive with the outer perimeters 160 and 162 of the conductive members 120 and 126 and are located inward of the outer edges 164 and 166 that define the outer perimeters 160 and 162. Turning to FIGS. 14-17, the holes 132 and anchors 134 are located between the windows 122 and 128 that are formed in the front layer 116 of the cuff body 110 and the outer perimeters 160 and 162 of the conductive members 120 and 126. The respective pluralities of anchors 134 are, therefore, coextensive with the window frames 124 and 130 and connect window frames to the rear layer 118 of the cuff body 110 by way of, i.e., by extending completely through, the associated portions of the conductive members 120 and 126.

There are a number of advantages associated with the exemplary conductive member holes 132 and the associated anchors 134. For example, as compared to an otherwise identical nerve cuff without the holes and anchors, the stress applied to the conductive members 120 and 126 when the nerve cuff 102 is in a furled state will be less likely to cause delamination at the relatively thin window frames 124 and 130 and/or dislodgement of the conductive members.

The exemplary cuff body 110 may be formed from any suitable material. Such materials may be biologically compatible, electrically insulative, elastic and capable of functioning in the manner described herein. The cuff materials should be pliable enough to allow a clinician to unfurl the cuff body 110 (and nerve cuff 102) and place the nerve cuff around the HGN trunk (or HGN GM branch). The exemplary materials should also be resilient enough to cause the nerve cuff body 110 (and nerve cuff 102) return to its pre-shaped furled state when the force is removed, yet flexible enough to allow the cuff body 110 (and nerve cuff 102) to instead assume the slightly larger, expanded and less tightly furled states, By way of example, but not limitation, suitable cuff body materials include silicone, polyurethane and styrene-isobutylene-styrene, (SIBS) elastomers. Suitable materials for the contacts 112 and 114 include, but are not limited to, platinum-iridium and palladium.

During one exemplary manufacturing process, the front layer 116 with the windows 122 and 128 is formed in a mold from silicone or other cuff body material. The conductive members 120 and 126, which have been previously connected to the wires 136, are placed into the mold over the front layer 116 with the conductive members aligned with the windows 122 and 128 and the holes aligned with the window frames 124 and 130. The rear layer 118 is then formed in the mold from silicone or other cuff body material over the front layer 116, the conductive members 120 and 136, and portions of the wires 136. The cuff body material (and, in some instances, adhesive) fills the holes 132, thereby forming the anchors 134 (FIGS. 14-17) that connect the relatively thin window frames 124 and 130 to the relatively thick rear layer 118 by way of, i.e., by extending completely through, the conductive members 120 and 126.

It should be noted that the present contacts, conductive members, cuff bodies and nerve cuffs are not limited to the exemplary embodiments described above. By way of example, the sizes, shapes and spacings of the conducive members and the windows (and, therefore, the contacts) and/or the holes that extend completely through the conductive members may be varied. To that end, the holes 132 in the conductive members 120 and 126 are circular in cross-section. The exemplary conductive member 126a illustrated in FIG. 18, on the other hand, includes a plurality spaced holes 132a that are rectangular in cross-section and extend completely through the conductive member. The holes 132a are coextensive with the outer perimeter 162a and are located inward of the outer edges 166a. One or more conductive members 126a may be incorporated into, for example, the exemplary nerve cuff 102 in place of one or more conductive members 126. Similar rectangular holes may be added to one or more of the conductive members 120. Alternating patterns of differently sized and shaped holes may also be employed.

Figures 18, 19, 20, 21, 22:
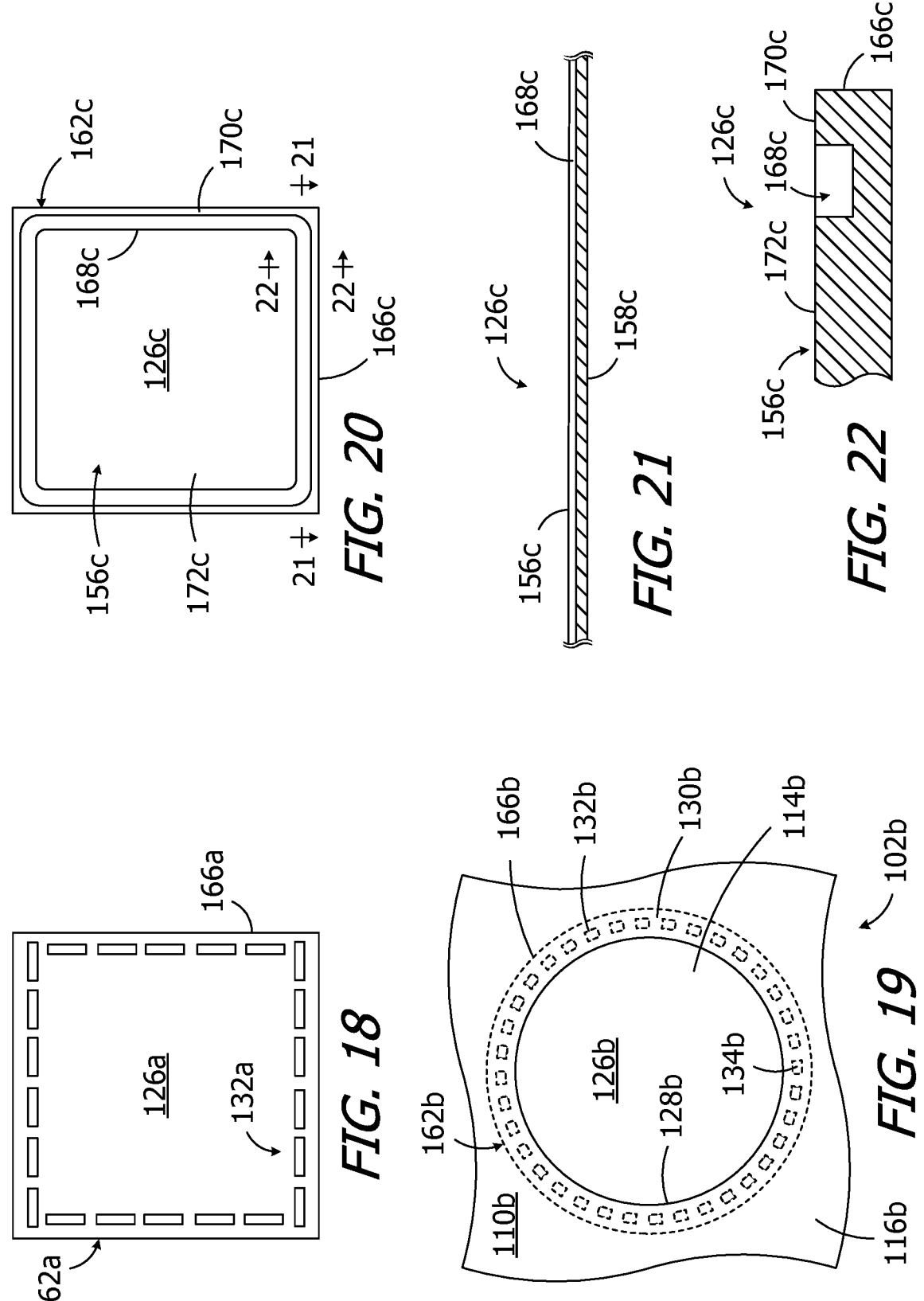
FIG. 18 is a front view of a conductive member in accordance with one embodiment of a present invention.
FIG. 19 is a front view of a portion of a nerve cuff in accordance with one embodiment of a present invention.
FIG. 20 is a front view of a conductive member in accordance with one embodiment of a present invention.
FIG. 21 is a section view taken along line 21-21 in FIG. 20.
FIG. 22 is a section view taken along line 22-22 in FIG. 20.

Turning to FIG. 19, and although only one contact is shown here, the exemplary nerve cuff 102b includes a plurality of circular contacts 114b are arranged in the same manner as the contacts 114 illustrated in FIGS. 5 and 6. In particular, the nerve cuff 102b includes a cuff body 110b with a front layer 116b and a rear layer (not shown) and a plurality of circular conductive members 126b. The front layer 116b includes circular windows 128b that expose portions of the conductive members 126b. The windows 128b are located inwardly of the circular outer perimeters 162b of the conductive members 126b that are defined by the circular edge 166b. The portions of the front layer 116 that are located between the windows 128b and the outer perimeters 162b of the conductive members 126b define annular window frames 130b that hold the conductive members 126b against the rear layer. A plurality of spaced arcuate holes 132, which are coextensive with the window frame 130b and inward of the edge 166b, extend completely through the conductive members 126b, from the front to the rear, and facilitate the formation of window frame anchors 134b in the manner described above.

Techniques, such as plasma, primer, and surface roughening may also be employed to improve adhesion and further reduce the likelihood of delamination as the nerve cuff is manipulated. With respect to primer, the present inventors have determined that it is advantageous to prevent primer applied to the surface of the conductive members that will be aligned with the window frames from entering the area that will be exposed by the windows. To that end, and referring to FIGS. 20-22, the exemplary conductive member 126c includes a channel 168c that is coextensive with the perimeter 162c and located inward of the side edges 166c. The channel 168c extends through the front side 156c toward (but not to) the rear side 158c. Primer may be applied to front side region 170c, typically all the way around the perimeter, to facilitate adhesion between the window frame and the conductive member 126c. The channel 168c will prevent the primer from spreading onto the front side region 172c that will be exposed by a window to define a contact.

Figures 23, 24, 25, 26:
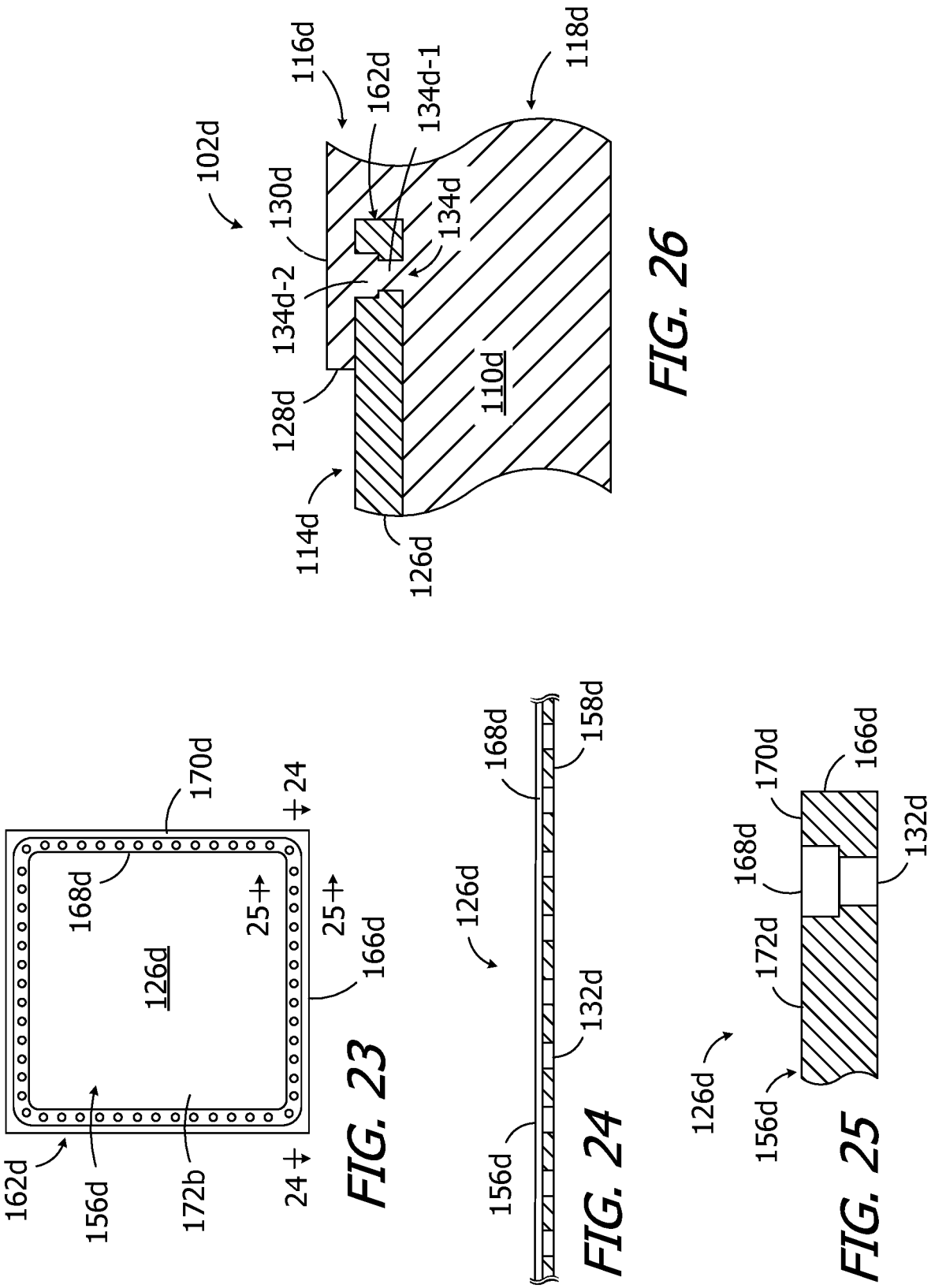
FIG. 23 is a front view of a conductive member in accordance with one embodiment of a present invention.
FIG. 24 is a section view taken along line 24-24 in FIG. 23.
FIG. 25 is a section view taken along line 25-25 in FIG. 23.
FIG. 26 is a section view of a portion of a nerve cuff in accordance with one embodiment of a present invention.

In some instances, a conductive member may include holes as well as a channel. To that end, the exemplary conductive member 126d illustrated in FIGS. 23-25 includes a channel 168d that is coextensive with the perimeter 162d, located inward of the side edges 166d, and extends through the front side 156d toward (but not to) the rear side 158d. The exemplary conductive member 126d also includes a plurality of holes 132d extend completely through the conductive member 126d, from the closed end of the channel 168d to the rear side 154d. The holes 132d will form the anchor portions, while the channel 168d advantageously prevents primer from spreading from the front side region 170d onto the front side region 172d and will also forms an anchor portion. Turning to FIG. 26, an exemplary nerve cuff 102d (partially shown) may include with a cuff body 110d and contacts 114d that are defined by conductive member 126d and windows 128d. The holes 132d and channel 168d facilitate the formation of an anchor 134d that includes a plurality of cylindrical anchor portions 134d-1 (in the holes 132d) and a continuous portion 134d-2 (in the channel 168d) that together extend from the front layer 116d to the rear layer 118d. The anchor 134d connects the window frames 124d associated with the contacts 114d to the rear layer 118d by way of, i.e., by extending completely through, the conductive members 126d.

With respect to dimensions, the exemplary nerve cuffs described herein are configured to accommodate HGN structures that have diameters of about 2.5 mm (e.g., the HGN GM branch 24), about 3.0 mm (e.g., the HON GM branch 24 in a swollen state), and about 4.0 mm (e.g., the HGN trunk 22). The plurality of contacts 112-1 and plurality of contacts 112-2 which, as noted above, each function as single relatively wide contact and are sized such that the relatively wide contacts will each extend completely around the inner lumen 174 (FIG. 9) defined by the nerve cuff, i.e., 360° or more around the longitudinal axis of the inner lumen, when the cuff body 110 is in the fully furled state that accommodates an HGN structure having a diameter of about 2.5 mm. Viewed as a group, the relatively narrow contacts 114 also will extend completely around the inner lumen 174 when the when the cuff body 110 is in the fully furled state. The relatively wide pluralities of contacts 112-1 and 112-2 will also extend substantially around the inner lumen 174, i.e., at least 288° in some examples and 360° or more in other examples, around the longitudinal axis of the inner lumen, when the cuff body 110 is in an expanded and less tightly furled state that accommodates an HGN structure having a diameter of about 4.0 mm, as will, when viewed as a group, the relatively narrow contacts 114.

Figures 27, 28:
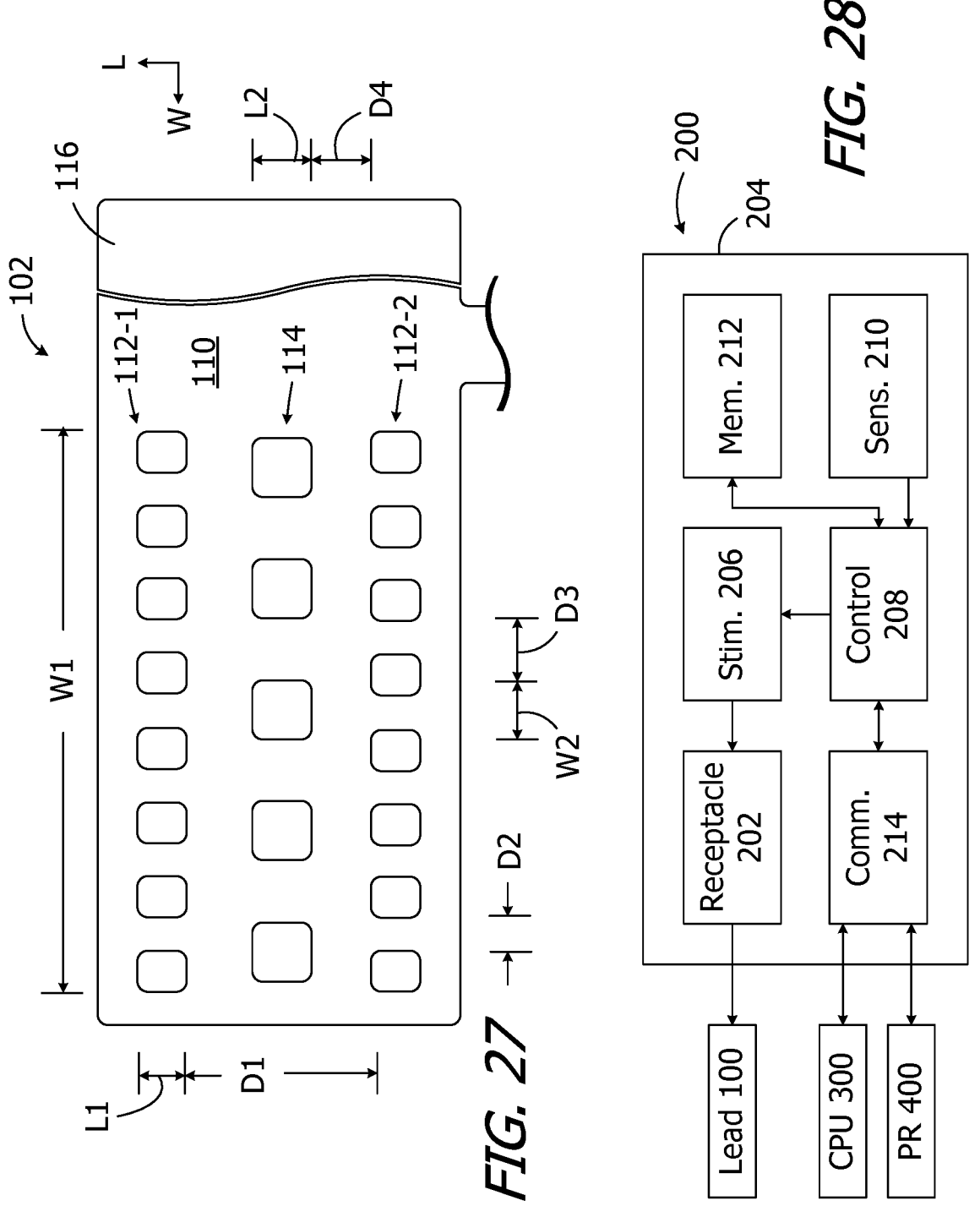
FIG. 27 is a front view of the nerve cuff illustrated in FIG. 1 in an unfurled state.
FIG. 28 is a block diagram of the stimulation system illustrated in FIG. 1.

The dimensions of the present nerve cuffs, including the various elements thereof, may by any dimensions that result in the nerve cuffs functioning as intended. With respect to the dimensions of the cuff body 110 of the exemplary nerve cuff 102, and referring to FIG. 5, the cuff body is about 1.1 inches wide and about 0.34 inches long. As used herein in the context of dimensions, the word "about" means ±10-20%. The width of the stimulation region 148 is about 0.6 inches, while the width of the compression region 150 is about 0.4 inches. The individual contacts 112 are same size, and the relatively narrow contacts 114 are the same size, in the illustrated implementation. In other implementations, the contacts 112 may be different sizes and/or the relatively narrow contacts 114 may be different sizes. Referring to FIG. 27, the width W1 of the total width each group of contacts 112-1 and 112-2 is about 0.5 inches, the length L1 is about 0.04 inches, the distance D1 between contacts 112-1 and contacts 112-2 is about 0.2 inches, and the distance D2 between adjacent contacts 112 is about 0.02 inches. The width W2 of the contacts 114 is about 0.07 inches, the length L2 is about 0.07 inches and the distance D3 between the contacts 114 is about 0.05 inches. The distance D3 may also be increased or decreased as desired to accomplish various stimulation objectives. The distance D4 between the contacts 114 and the contacts 112-1 and 112-2 is about 0.06 inches.

Turning to FIG. 28, the exemplary IPG 200 includes the aforementioned receptacle 202, a hermetically sealed outer case 204, and various circuitry (e.g., stimulation circuitry 206, control circuitry 208, sensing circuitry 210, memory 212, and communication circuitry 214) that is located within the outer case 204. The outer case 204 may be formed from an electrically conductive, biocompatible material such as titanium. The stimulation circuitry 206, which is coupled to the contacts 112 and 114 by way of the connector 106, receptacle 202 and wires 136, is configured to deliver stimulation energy to the HGN. The control circuitry 208 controls when and for how long the stimulation circuitry 206 applies stimulation, the intensity of the stimulation, the mode of stimulation (i.e., monopolar, bipolar or tripolar), and the particular contacts that are used in the stimulation. In the monopolar stimulation, at least a portion of the outer case 204 functions as a return electrode, in the electrical circuit that also includes one or more of the contacts 112 and 114. In bipolar stimulation, the outer case 204 is not part of the electrical circuit and current instead flows from one of the contacts 112 and 114 to one of the other contacts 112 and 114. In tripolar stimulation, the outer case 204 is not part of the electrical circuit and current flows from one or more of the contacts 112 and 114 to more than one of the other contacts 112 and 114. The contacts that the current flows to form part of the return path for the stimulation energy, as do the associated wires connected thereto. The stimulation may also be predominantly axial vector stimulation, predominantly radial vector stimulation, or a hybrid of axial vector and radial vector.

It should also be noted here that in most instances, contacts that are entirely separated from (and electrically disconnected from) the associated nerve by the cuff body will not be used by the IPG for current transmission and return. Such contacts may be identified by, for example, measuring the impedance at each contact.

The sensing circuitry 210 in the illustrated embodiment may be connected to one or more sensors (not shown) that are contained within the outer case 204. Alternatively, or in addition, the sensors may be affixed to the exterior of the outer case 204 or positioned at a remote site within the body and coupled to the IPG 200 with a connecting lead. The sensing circuitry 210 can detect physiological artifacts that are caused by respiration (e.g., motion or ribcage movement), which are proxies for respiratory phases, such as inspiration and expiration or, if no movement occurs, to indicate when breathing stops. Suitable sensors include, but are not limited to, inertial sensors, bioimpedance sensors, pressure sensors, gyroscopes, ECG electrodes, temperature sensors, GPS sensors, and combinations thereof. The memory 212 stores data gathered by the sensing circuitry 210, programming instructions and stimulation parameters. The control circuitry 208 analyzes the sensed data to determine when stimulation should be delivered. The communication circuitry 214 is configured to wirelessly communicates with the clinician's programming unit 300 and patient remote 400 using radio frequency signals.

The control circuitry 208 may apply stimulation energy to either the HGN truck or an HGN branch (e.g. the HGN GM branch) in various stimulation methodologies by way of the cuff 102 when the patient is in the inspiratory phase of respiration, and other conditions for stimulation are met, thereby causing anterior displacement of the tongue to keep the upper airway unobstructed. The control circuitry 208 causes the stimulation circuitry 206 to apply stimulation in the form of a train of stimulation pulses during these inspiratory phases of the respiratory cycle (or slightly before the inspiration and ending at the end of inspiration) and not the remainder of the respiration cycle. The train of stimulus pulses may be set to a constant time duration or may change dynamically based on a predictive algorithm that determines the duration of the inspiratory phase of the respiratory cycle.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions. The inventions include any and all combinations of the elements from the various embodiments disclosed in the specification. The scope of the present inventions is limited solely by the claims set forth below.

We claim:

1. An electrode lead, comprising:
  an elongate lead body having a proximal end and a distal
    end; and
  a nerve cuff including
    a biologically compatible, elastic, electrically insula-
      tive cuff body affixed to the distal end of the lead
      body, the cuff body configured to be circumferen-
      tially disposed around a nerve, having a pre-set
      furled state that defines an inner lumen, being mov-
      able to an unfurled state, including a front layer and
      a rear layer, and defining a length and a width in the
      unfurled state that is greater than the length,
    a plurality of electrically conductive members located
      between the front and rear layers of the cuff body,
      each electrically conductive member defining a front
      side, a rear side and an outer perimeter and including
      a plurality of holes that extend from the front side to
      the rear side and that are located around the outer
      perimeter, and a plurality of electrical conductors extending through the lead body from at least some of the electrically conductive members to the proximal end of the lead body, wherein the cuff body front layer includes a plurality of windows that are respectively aligned with and located inwardly of the outer perimeters of the electrically conductive members, and a plurality of window frames that extend from the windows to the outer perimeters of the electrically conductive members, and wherein the cuff body includes a plurality of anchors that respectively extend through the electrically conductive member holes and connect the window frames to the cuff body rear layer.

2. An electrode lead as claimed in claim 1, wherein at least some of the electrically conductive members are electrically connected to one another in series.

3. An electrode lead as claimed in claim 1, wherein at least some of the holes are circular in cross-section.

4. An electrode lead as claimed in claim 1, wherein at least some of the holes not circular in cross-section.

5. An electrode lead as claimed in claim 1, wherein at least some of the electrically conductive members include four side edges that define the perimeter; and there are a plurality of holes adjacent to each of the side edges.

6. An electrode lead as claimed in claim 1, wherein at least some of the electrically conductive members include a single curved side edge that defines the perimeter; and there are a plurality of holes adjacent to the entire curved side edge.

7. An electrode lead, comprising:

an elongate lead body having a proximal end and a distal end; and a nerve cuff including a biologically compatible, elastic, electrically insulative cuff body affixed to the distal end of the lead body, the cuff body configured to be circumferentially disposed around a nerve, having a pre-set furled state that defines an inner lumen, being movable to an unfurled state, including a front layer and a rear layer, and defining a length and a width in the unfurled state that is greater than the length, a plurality of electrically conductive members located between the front and rear layers of the cuff body, each electrically conductive member defining a front side, a rear side and an outer perimeter and including a channel that extends from the front side toward, but not to, the rear side and that is coextensive with the outer perimeter, and a plurality of electrical conductors extending through the lead body from at least some of the electrically conductive members to the proximal end of the lead body, wherein the cuff body front layer includes a plurality of windows that are respectively aligned with and located inwardly of the outer perimeters of the electrically conductive members such that portions of the electrically conductive members located inwardly of the windows are exposed to the inner lumen.

8. An electrode lead as claimed in claim 7, wherein at least some of the electrically conductive members are electrically connected to one another in series.

9. An electrode lead as claimed in claim 7, wherein at least some of the electrically conductive members includes side edges that define the outer perimeter; and the channels is inwardly of the side edges.

10. An electrode lead as claimed in claim 7, wherein the channels each define an open end, that is aligned with the contact member front side, and a closed end; and at least some of the electrically conductive members include a plurality of holes that extend from the closed end of channels to the rear side of the electrically conductive members.

11. An electrode lead as claimed in claim 10, wherein the cuff body front layer includes a plurality of window frames that extend from the windows to the outer perimeters of the electrically conductive members; and the cuff body includes a plurality of anchors respectively associated with the plurality of window frames that connect the window frames to the cuff body rear layer.

12. An electrode lead as claimed in claim 10, wherein the anchors each include a first portion that is located within the channel of the associated electrically conductive member and a plurality of second portions that are located within the holes of the associated electrically conductive member.

* * * * *